US00PP31978P2

(12) United States Plant Patent
Van Swieten

(10) Patent No.: US PP31,978 P2
(45) Date of Patent: Jul. 14, 2020

(54) ***PHALAENOPSIS* ORCHID PLANT NAMED 'PHALFITYJA'**

(50) Latin Name: ***Phalaenopsis* hybrid**
Varietal Denomination: PHALFITYJA

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,972

(22) Filed: Jul. 12, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALFITYJA', particularly characterized by having reddish-purple flowers with light purple centers, small white edges, and red-purple lips, 1 to 3 peduncles that are short and moderate, leaves that are oblong, and is propagated by meristem tissue culture, is disclosed.

3 Drawing Sheets

Genus and species: *Phalaenopsis* hybrid.
Variety denomination: 'PHALFITYJA'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFITYJA'.

The new *Phalaenopsis* plant is a product of a planned breeding program conducted by the inventor in Bleiswijk, the Netherlands. The objective of this breeding program was to create a new *Phalaenopsis* plant with numerous attractive small, reddish-purple flowers with light purple centers, small white edges, and red-purple lips, suitable for potted plant production.

The new *Phalaenopsis* plant 'PHALFITYJA' is a result of cross-pollination made by the inventor in November 2007 in Bleiswijk, the Netherlands, of the proprietary female, or seed parent, *Phalaenopsis* hybrid '01-1789' (unpatented) with the proprietary male, or pollen parent, *Phalaenopsis* hybrid 'PHALDOMEO' (U.S. Plant Pat. No. 25,682).

The new *Phalaenopsis* was selected by the inventor as a single plant within the progeny of the stated cross-pollination in a controlled greenhouse in Bleiswijk, the Netherlands, in November 2010. Asexual reproduction of the new *Phalaenopsis* plant by meristem tissue culture since 2013 in Bleiswijk, the Netherlands, has demonstrated that the new variety reproduces true to type with all of the characteristics, as herein described, firmly fixed and retained through successive generations.

Plant Breeder's Rights for this variety have been applied for in the European Union on Sep. 28, 2017, by Applicant who obtained the subject matter disclosed directly from the Inventor. 'PHALFITYJA' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, the Netherlands, and can be used to distinguish 'PHALFITYJA' as a new and distinct variety of *Phalaenopsis* plant:

1) Reddish-purple flowers with light purple centers, small white edges, and red-purple lips;
2) 1 to 3 peduncles;
3) Peduncle is short and moderate; and
4) Shape of the leaf is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2019. Colors in the photographs may differ from the color values cited in the detailed botanical description, which accurately describe the actual colors of the new variety.

DESCRIPTION OF THE NEW VARIETY

Figure 1:
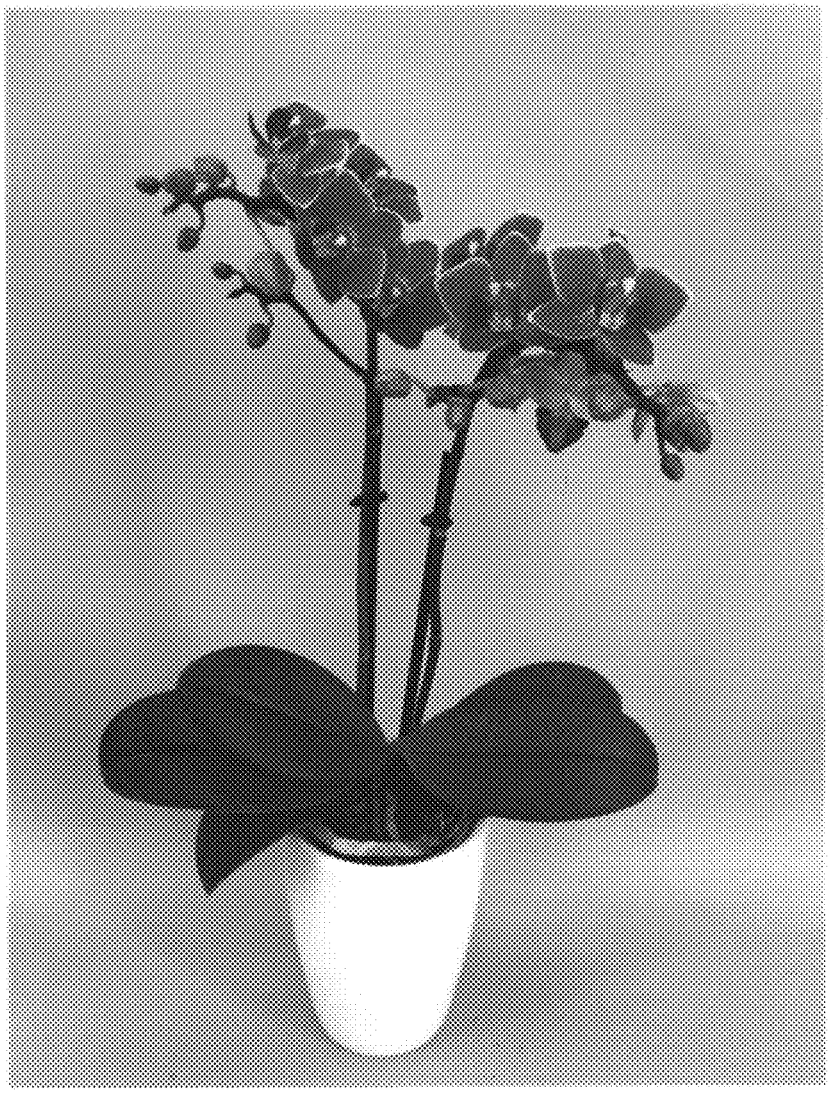
FIG. 1 shows the overall plant habit, including blooms, buds, and foliage of 'PHALFITYJA'.
Figure 2:
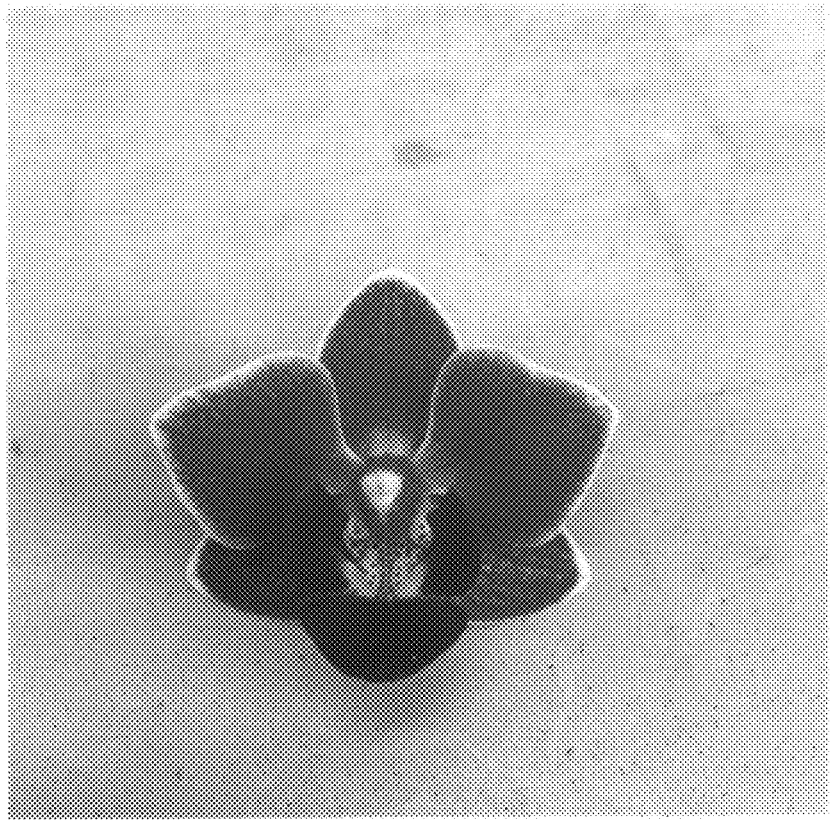
FIG. 2 shows a close-up of a flower of 'PHALFITYJA'.
Figure 3:
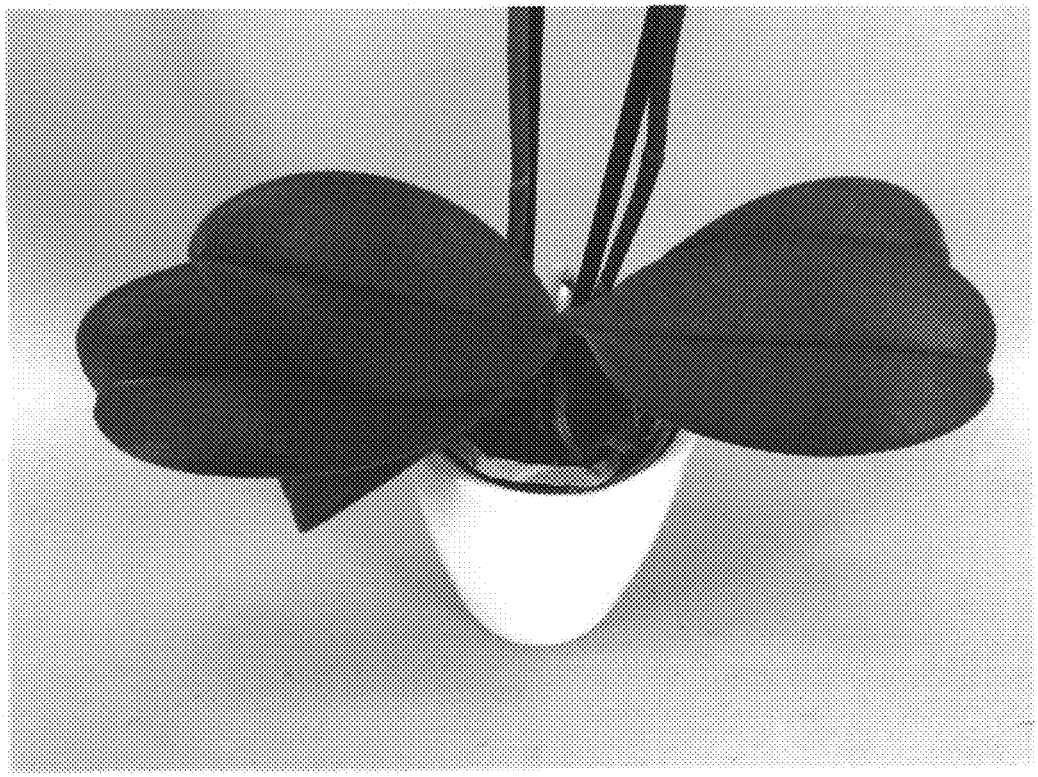
FIG. 3 shows an overhead view of the leaves of 'PHALFITYJA'.

The following detailed description sets forth the distinctive characteristics of 'PHALFITYJA'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2019 on flowering plants which were planted in 6-centimeter (diameter) pots. After in-vitro propagation, the plants were directly transplanted into 6-centimeter pots and grown in a greenhouse between 27° C. to 29° C. for 32 weeks, continued by a cooling period of 6 weeks between 18° C. to 20° C. and 12 weeks in a greenhouse of 21° C. Flowering occurs after 50 weeks in 6-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFITYJA'.

Parentage:

*Female parent*.—*Phalaenopsis* cultivar '01-1789' (unpatented).

*Male parent*.—*Phalaenopsis* cultivar 'PHALDOMEO' (U.S. Plant Pat. No. 25,682).

Propagation:

*Type*.—Meristem tissue culture.

Roots:

*Root description*.—Greyed-green (between RHS 190B and 190C) colored roots with branching lateral roots having yellow-green (RHS 144C) colored root tips.

Plant:

*Commercial crop time to flowering*.—Following asexual propagation (in-vitro), the plants are directly transplanted into 6-centimeter pots and the plants are finished after 48 to 50 weeks.

*Growth habit of peduncle*.—Upright to slightly pendant with panicle inflorescence.

*Height (from soil level to top of inflorescence)*.—Approximately 23.0 cm to 28.0 cm.

*Width (measured from leaf tips)*.—About 19.0 cm to 21.0 cm.

*Vigor*.—Moderate.

Leaves:

*Mature leaves*.—Quantity per plant: 8 to 10 leaves are produced before flowering. Length (fully expanded): 9.0 cm to 11.0 cm. Width: 4.0 cm to 5.0 cm. Shape: Oblong. Base shape: Moderately elongated. Apex: Obtuse unequal. Leaf blade angle with the petiole (measured from the horizontal position): Between 20 degrees and 35 degrees. Leaf margin: Entire. Color: Upper surface: RHS 146A. Lower surface: RHS 146B. Texture (both upper and lower surfaces): Rough. Thickness: 1.8 mm to 2.2 mm. Variegation: Absent. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—13 to 18.

*Length*.—23.0 cm to 28.0 cm.

*Diameter*.—3.0 mm to 4.0 mm.

*Strength*.—Strong.

*Aspect*.—Upright to slightly pendant.

*Texture*.—Smooth.

*Color*.—Mix of green (RHS 146B) and brown (RHS N200A).

*Internode length*.—2.0 cm to 3.0 cm.

Inflorescence description:

*Appearance*.—Upright to slightly pendant, panicle inflorescence with bilaterally symmetrical flowers that open in succession beginning with the lowermost flower.

*Number of inflorescences*.—1 to 3.

*Inflorescence size*.—Height (from base to tip): 80.0 mm to 120.0 mm.

*Flowering time*.—First flowers can be expected 10 to 11 months after planting in a 6-cm pot.

*Flower*.—Height: 30.0 mm to 35.0 mm. Diameter: 35.0 mm to 40.0 mm. Depth of lip: 14.0 mm to 16.0 mm.

*Flower longevity*.—On the plant: 8 to 13 weeks.

*Fragrance*.—Absent.

*Flower bud*.—Average size: Medium. Length: 13.0 mm to 15.0 mm. Width: 11.0 mm to 13.0 mm. Shape: Egg shaped. Color: Yellow-green (between RHS 145B and 145C) at the base and purplish-red (RHS N77B) toward the tip.

*Petals*.—Arrangement: Open/free. Shape: Semi-circular. Apex: Obtuse asymmetric. Margin: Slightly undulated. Length (from base to tip): 16.0 mm to 18.0 mm. Width: 16.0 mm to 18.0 mm. Position of the broadest part of the petal: At the base. Color (when fully opened): Upper surface: Basic color: Reddish-purple (RHS N78A). Over color: Light reddish-purple (RHS N78D) and small white edge (RHS NN155C). Lower surface: Basic color: Purplish-pink (RHS N78C). Over color: Light purple (RHS 76A) at the base.

*Dorsal sepal*.—Shape: Elliptic. Apex: Obtuse symmetric. Margin: Entire. Length (from base to tip): 18.0 mm to 20.0 mm. Width: 12.0 mm to 14.0 mm. Color (when fully opened): Upper surface: Basic color: Reddish-purple (RHS N78A). Over color: Light reddish-purple (RHS N78D) at the base and white edge (RHS NN155C). Lower surface: Basic color: Reddish-purple (RHS N78D). Over color: White edge (RHS NN155C).

*Lateral sepals*.—Shape: Ovate. Apex: Obtuse asymmetric. Margin: Entire. Length (from base to tip): 18.0 mm to 20.0 mm. Width: 12.0 mm to 14.0 mm. Color (when fully opened): Upper surface: Basic color: Reddish-purple (RHS N78A). Over color: Greenish-white (RHS 155C) and dotted at the base (RHS 72A); white edge (RHS NN155C). Lower surface: Basic color: Light reddish-purple (RHS N78D). Over color: Greenish-white (RHS 155C) at the base; white edge (RHS NN155C) and reddish-purple midvein (RHS N78B) toward the tip.

*Labellum (lip)*.—Whiskers: Present. Length of whiskers: 1.0 mm to 2.0 mm. Color of whiskers: Dark purplish-red (RHS N79C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated. Length: 11.0 mm to 13.0 mm. Width: 7.0 mm to 9.0 mm. Color: Yellow (RHS 8A to 8B) and dotted (RHS 185A) at the base; dark red (RHS 59A) and dark purplish-red (RHS N79C) toward margin.

*Apical lobe*.—Shape: Ovate. Margin: Entire. Length: 12.0 mm to 14.0 mm. Width: 13.0 mm to 15.0 mm. Color: Slightly yellow (RHS 8A) at the base; dark red (RHS 59A) in the middle and dark purplish-red (RHS N79C) toward the margin.

*Callus*.—Average size: Small. Height: 3.0 mm to 4.0 mm. Length: 3.0 mm to 4.0 mm. Width: 2.0 mm to 3.0 mm. Color: Yellow (RHS 8A); dotted (RHS 183B).

Reproductive organs:

*Column*.—Length: 6.0 mm to 8.0 mm. Diameter: 3.0 mm to 4.0 mm. Color: Reddish-purple (RHS N78A).

*Pollinia*.—Quantity: 2. Diameter: 0.6 mm to 0.8 mm. Color: Orange (RHS 25A).

*Ovary*.—Length: 5.0 mm to 7.0 mm. Diameter: 1.2 mm to 1.4 mm. Color: Very light purple (RHS 76B) toward the flower.

*Pedicel*.—Length: 21.0 mm to 23.0 mm. Diameter: 1.4 mm to 1.6 mm. Color: Slightly light yellow-green (RHS 145B) at the base; light yellow-green (RHS 145D) and very light purple (RHS 76B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent of 'PHALFITYJA', cultivar '01-1789' (unpatented) is no longer in existence, therefore a meaningful comparison cannot be made.

'PHALFITYJA' differs from male parent plant 'PHALDOMEO' (U.S. Plant Pat. No. 25,682) in that 'PHALFITYJA' has obtuse leaf apexes, whereas 'PHALDOMEO' has mucronate leaf apexes. Additionally, 'PHALFITYJA' has shorter apical lobes than 'PHALDOMEO'.

'PHALFITYJA' is most similar to the commercial *Phalaenopsis* plants named 'PHALFUFLY' (U.S. Plant Pat. No. 31,024) and 'PHALFEMYM' (U.S. Plant Pat. No. 29,783). 'PHALFITYJA' differs from the commercial variety 'PHALFUFLY' in that 'PHALFITYJA' has obtuse dorsal sepal apexes, weakly spatulate lateral lobes, and whiskers, whereas 'PHALFUFLY' has rounded to slightly emarginated dorsal sepal apexes, spatulate lateral lobes, and no whiskers.

'PHALFITYJA' differs from the commercial variety 'PHALFEMYM' in that 'PHALFITYJA' has smaller flowers, narrower petals, and narrower dorsal sepals than 'PHALFEMYM'.

I claim:

1. A new and distinct variety of *Phalaenopsis* plant named 'PHALFITYJA', substantially as described and illustrated herein.

* * * * *